(12) United States Patent
Howard

(10) Patent No.: US 10,220,215 B2
(45) Date of Patent: Mar. 5, 2019

(54) FAR-FIELD SHORT-RANGE RADIO-FREQUENCY ANTENNA ON THE SIDE OF AN IMPLANTABLE MEDICAL DEVICE CASE

(71) Applicant: Boston Scientific Neuromodulation Corporation, Valencia, CA (US)

(72) Inventor: Joshua D. Howard, Winnetka, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/424,284

(22) Filed: Feb. 3, 2017

(65) Prior Publication Data

US 2017/0281957 A1    Oct. 5, 2017

Related U.S. Application Data

(60) Provisional application No. 62/314,726, filed on Mar. 29, 2016.

(51) Int. Cl.
*A61N 1/372*  (2006.01)
*A61N 1/375*  (2006.01)

(52) U.S. Cl.
CPC ....... *A61N 1/37229* (2013.01); *A61N 1/3754* (2013.01)

(58) Field of Classification Search
None
See application file for complete search history.

(56) References Cited

U.S. PATENT DOCUMENTS

| | | |
|---|---|---|
| 4,127,110 A | 11/1978 | Bullara |
| 4,681,111 A | 7/1987 | Silvian |
| 5,058,581 A | 10/1991 | Silvian |
| 5,342,408 A | 8/1994 | Decoriolis et al. |
| 5,562,713 A | 10/1996 | Silvian |
| 5,861,019 A | 1/1999 | Sun et al. |
| 5,912,648 A | 6/1999 | Walthers |
| 5,995,052 A | 11/1999 | Sadler et al. |

(Continued)

FOREIGN PATENT DOCUMENTS

| | | |
|---|---|---|
| EP | 1166820 | 9/2009 |
| WO | 2005/123186 | 12/2005 |

(Continued)

*Primary Examiner* — Brian T Gedeon
(74) *Attorney, Agent, or Firm* — Lewis & Reese, PLLC

(57) ABSTRACT

An Implantable Medical Device (IMD) is disclosed having a bi-directional short-range far-field Radio-Frequency (RF) data antenna, operable in accordance with a short-range RF standard such as Bluetooth for example. The antenna is neither located inside the conductive case of the IMD, nor in the non-conductive header of the IMD that includes the lead connectors. Instead, the antenna is outside of the case, proximate to and generally planar with a flat planar side of the case that faces outward of the patient when the IMD is implanted. Dielectric materials keep the antenna from shorting to the case and to the patient's tissue. Because the antenna is not located within the conductive case, data communications to and from the antenna are less subject to attenuation. Not locating the antenna in the header reserves room for the header's lead connectors, thus simplifying IMD design.

18 Claims, 5 Drawing Sheets

(56) References Cited

U.S. PATENT DOCUMENTS

| | | |
|---|---|---|
| 6,008,762 A | 12/1999 | Nghiem |
| 6,054,955 A | 4/2000 | Schlegel, Jr. et al. |
| 6,133,890 A | 10/2000 | Damiani |
| 6,147,652 A | 11/2000 | Sekine |
| 6,218,992 B1 | 4/2001 | Sadler et al. |
| 6,240,317 B1 | 5/2001 | Villaseca et al. |
| 6,259,418 B1 | 7/2001 | Jones et al. |
| 6,285,336 B1 | 9/2001 | Zimmerman |
| 6,317,099 B1 | 11/2001 | Zimmerman et al. |
| 6,342,857 B1 | 1/2002 | Lane |
| 6,379,300 B1 | 4/2002 | Haubrich |
| 6,437,745 B1 | 8/2002 | Vaisanen et al. |
| 6,456,256 B1 | 9/2002 | Amundson et al. |
| 6,587,698 B1 | 7/2003 | Dosch |
| 6,603,432 B2 | 8/2003 | Hill et al. |
| 6,664,931 B1 | 12/2003 | Nguyen et al. |
| 6,850,803 B1 | 2/2005 | Jimenez et al. |
| 7,089,059 B1 | 8/2006 | Pless |
| 7,289,855 B2 | 10/2007 | Nghiem et al. |
| 7,309,262 B2 | 12/2007 | Zart et al. |
| 7,363,087 B2 | 4/2008 | Nghiem et al. |
| 7,467,014 B2 * | 12/2008 | Fuller ................ A61N 1/37229 607/36 |
| 7,554,493 B1 | 6/2009 | Rahman |
| 8,983,615 B2 | 3/2015 | Tahmasian et al. |
| 9,186,518 B2 | 11/2015 | Kothandaraman |
| 2003/0216793 A1 * | 11/2003 | Karlsson ............ A61N 1/37229 607/60 |
| 2006/0020300 A1 | 1/2006 | Nghiem et al. |
| 2006/0122665 A1 | 6/2006 | Nghiem et al. |
| 2006/0122666 A1 | 6/2006 | Nghiem et al. |
| 2006/0241724 A1 * | 10/2006 | Dublin ............... A61N 1/37223 607/60 |
| 2007/0060955 A1 | 3/2007 | Strother et al. |
| 2007/0135855 A1 * | 6/2007 | Foshee ................ A61B 5/0031 607/31 |
| 2007/0190866 A1 | 8/2007 | Zart et al. |
| 2009/0240309 A1 | 9/2009 | Rahman |
| 2010/0161002 A1 * | 6/2010 | Aghassian ......... A61N 1/37229 607/60 |
| 2015/0073498 A1 | 3/2015 | Kothandaraman |
| 2015/0073500 A1 | 3/2015 | Kothandaraman et al. |
| 2015/0231402 A1 | 8/2015 | Aghassian |
| 2015/0360038 A1 | 12/2015 | Zottola et al. |
| 2016/0051825 A1 | 2/2016 | Ter-Petrosyan et al. |
| 2016/0126771 A1 | 5/2016 | Aghassian et al. |
| 2016/0263385 A1 | 9/2016 | Aghassian |
| 2016/0274752 A1 | 9/2016 | Zhu et al. |

FOREIGN PATENT DOCUMENTS

| | | |
|---|---|---|
| WO | 2006/060750 | 6/2006 |
| WO | 2006/131302 | 12/2006 |
| WO | 2007/136657 | 11/2007 |
| WO | 2008/094783 | 8/2008 |

* cited by examiner

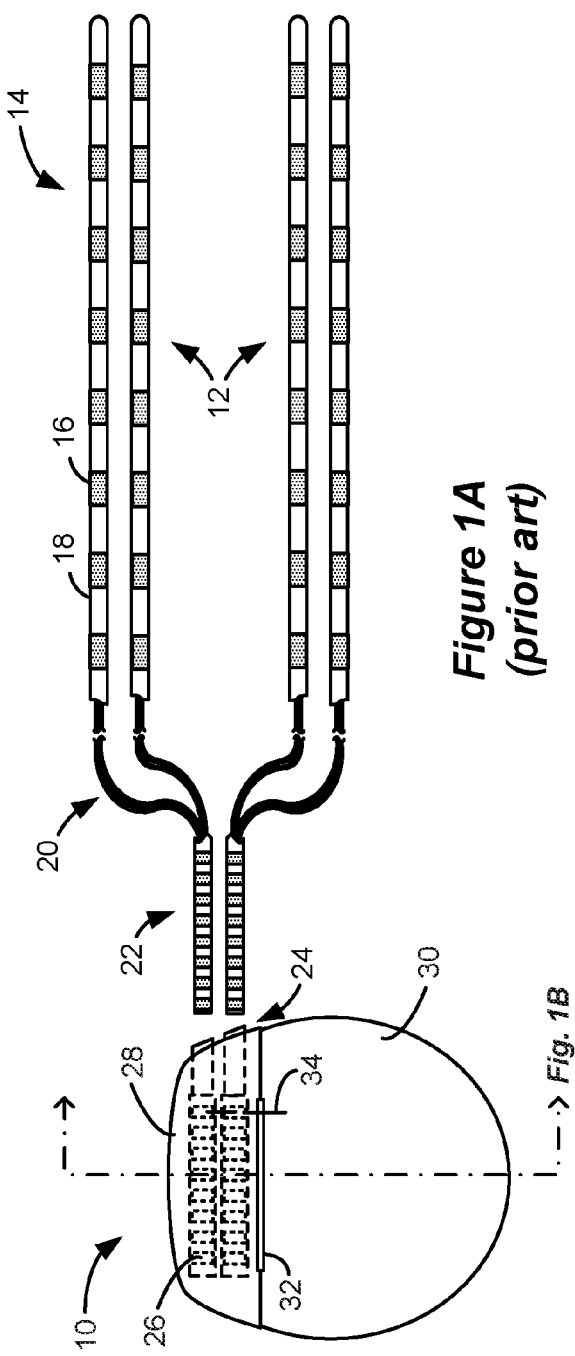
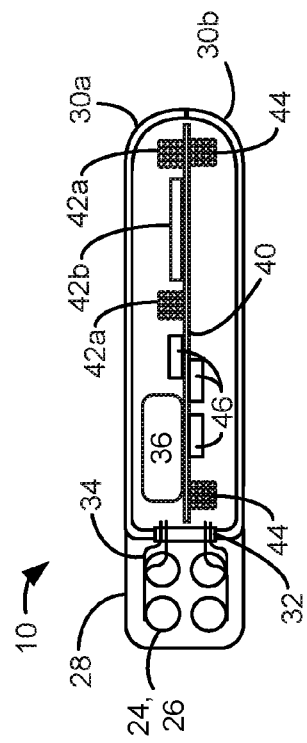
*Figure 1A (prior art)*
*Figure 1B (prior art)*

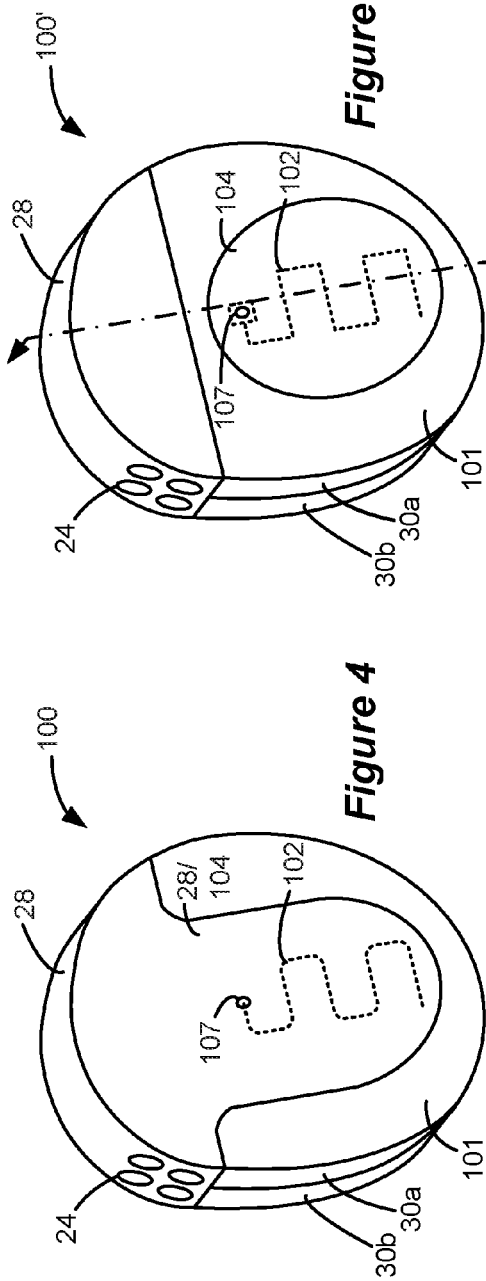
Figure 4
Figure 5A
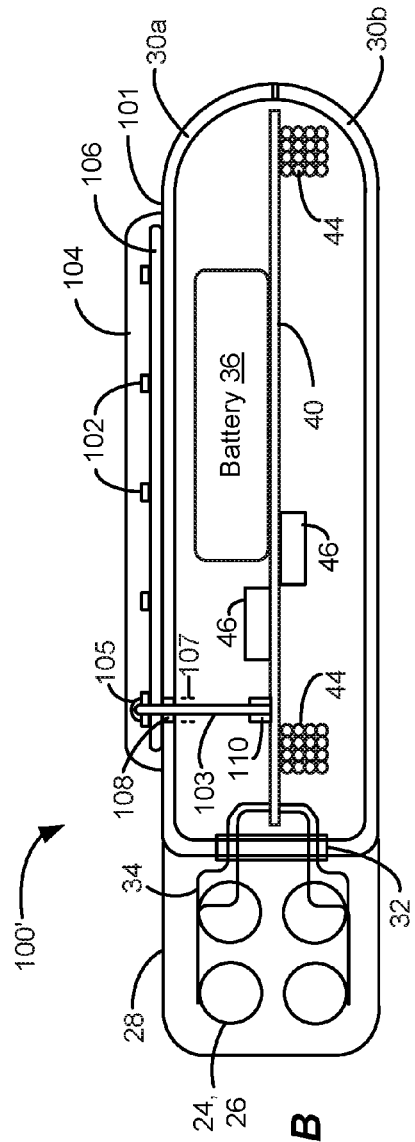
Figure 5B

FAR-FIELD SHORT-RANGE RADIO-FREQUENCY ANTENNA ON THE SIDE OF AN IMPLANTABLE MEDICAL DEVICE CASE

CROSS REFERENCE TO RELATED APPLICATIONS

This is a non-provisional application of U.S. Provisional Patent Application Ser. No. 62/314,726, filed Mar. 29, 2016, which is incorporated by reference in its entirety, and to which priority is claimed.

FIELD OF THE INVENTION

The present invention relates generally to implantable medical device systems, and more particularly to data antenna designs usable with an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. 6,516,227. However, the present invention may find applicability with any Implantable Medical Device (IMD) or in any IMD system.

An SCS system typically includes an Implantable Pulse Generator (IPG) 10 shown in plan and cross-sectional views in FIGS. 1A and 1B. The IMD 10 (more generally IMD 10) includes a biocompatible device case 30 that holds the circuitry and battery 36 (FIG. 1B) necessary for the IPG to function. The IMD 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in and encompassed by a header 28 on the IMD 10, which header can comprise an epoxy for example. Once inserted, the proximal contacts 22 connect to header contacts 26 in the lead connectors 24, which are in turn coupled by electrode feedthrough pins 34 through an electrode feedthrough 32 to circuitry within the case 30 (connection not shown). Case 30 can be formed of case portions 30a and 30b (FIG. 1B) which are laser welded together and to the electrode feedthrough 32.

In the illustrated IMD 10, there are thirty-two lead electrodes (E1-E32) split between four leads 14, with the header 28 containing a 2×2 array of lead connectors 24 to receive the leads' proximal ends. However, the number of leads and electrodes in an IPG is application specific and therefore can vary. In a SCS application, the electrode leads 14 are typically implanted proximate to the dura in a patient's spinal cord, and when a four-lead IMD 10 is used, these leads can be split with two on each of the right and left sides of the dura. The proximal electrodes 22 are tunneled through the patient's tissue to a distant location such as the buttocks where the IPG case 30 is implanted, at which point they are coupled to the lead connectors 24. A four-lead IMD 10 can also be used for Deep Brain Stimulation (DBS) in another example. In other IPG examples designed for implantation directly at a site requiring stimulation, the IPG can be lead-less, having electrodes 16 instead carried by the case of the IPG for contacting the patient's tissue.

As shown in the cross section of FIG. 1B, the IMD 10 includes a printed circuit board (PCB) 40. Electrically coupled to the PCB 40 are the battery 36, which in this example is rechargeable; other circuitry 46 coupled to top and/or bottom surfaces of the PCB, including a microcontroller and other circuitry necessary for IMD operation; a telemetry antenna—42a and/or 42b—for wirelessly communicating with an external device (FIGS. 2A and 2B); a charging coil 44 for wirelessly receiving a magnetic charging field from an external charger (not shown) for recharging the battery 36; and the electrode feedthrough pins 34 (connection to circuitry not shown). If battery 36 is permanent and not rechargeable, charging coil 44 would be unnecessary.

Both of telemetry antennas 42a and 42b can be used to transcutaneously communicate data through the patient's tissue to an external device, but are different in shape and in the electromagnetic fields they employ. Telemetry antenna 42a comprises a coil, which can bi-directionally communicate with an external device via a magnetic induction communication link, which comprises a magnetic field of typically less than 10 MHz operable in its near-field to communicate at a distance of 12 inches or less for example. Circuitry 46 would include telemetry circuitry coupled to the coil antenna 42a, including driver circuitry for energizing the coil antenna 42a to transmit data and receiver circuitry for resolving data received at the coil 42a. Such telemetry circuitry also operates in accordance with a modulation scheme (defining how data to be transmitted is modulated, and will be demodulated when received) and a communication protocol (defining the manner in which the data is formatted). A typical modulation scheme used for magnetic induction communications via coil antenna 42a is Frequency Shift Keying (FSK), although other modulation schemes could also be used.

Telemetry antenna 42b comprises a short-range Radio-Frequency (RF) antenna that operates in accordance with a short-range RF communication standard and its underlying modulation scheme and protocol to bi-directionally communicate with an external device along a short-range RF communication link. Short-range RF communication link typically operates using far-field electromagnetic waves ranging from 10 MHz to 10 GHz or so, and allows communications between devices at distances of about 50 feet or less. Short-range RF standards operable with antenna 42b include, for example, Bluetooth, BLE, NFC, Zigbee, WiFi (802.11x), and the Medical Implant Communication Service or the Medical Device Radiocommunications Service (both collectively referred to herein as "MICS" for short). Short-range RF antenna 42b can take any number of well-known forms for an electromagnetic antenna, such as patches, slots, wires, etc., and can operate as a dipole or a monopole. Circuitry 46 would include telemetry circuitry coupled to the short-range RF antenna 42b, again including driver and receiver circuitry.

IMD 10 could contain both the coil antenna 42a and the short-range RF antenna 42b to broaden the types of external devices with which the IMD 10 can communicate, although IMD 10 may also include only one of antenna 42*a* and 42*b*.

Examples of different external devices operable to communicate with the IMD 10 are shown in FIGS. 2A and 2B. Such external devices are typically used to adjust the therapy settings the IMD 10 will provide to the patient—such as which electrodes 16 are active to issue pulses; whether such electrodes sink or source current (i.e., polarity); the duration, frequency, and amplitude of pulses, etc.—which settings together comprise a stimulation program for the patient. External devices can also act as receivers of data from the IMD 10, such as various data reporting on the IMD's status and the level of the IMD's battery 36.

An external device having such functionality is shown first in FIG. 2A in the form of a patient remote control 50. Remote control (RC) 50 is typically hand-held, portable, and powered by a battery (not shown) within the RC's housing 51, which battery may be a primary battery or rechargeable. The RC 50 includes a Graphical User Interface (GUI) 53 similar to that used for a cell phone, including buttons 52 and a screen 54, and may have other user interface aspects as well, such as a speaker. The RC 50 also includes within its housing 51 communication means, including a coil antenna 59*a* and/or a short-range RF antenna 59*b*, which are respectively compatible with a coil antenna 42*a* or a short-range RF antenna 42*b* usable in the IMD 10. Similar to the IMD 10, RC 50 can have either or both of the antennas 59*a* and 59*b*. Processing in the RC 50 is controlled via a microcontroller 56, which would couple to telemetry circuitry coupled to either or both of the antennas 59*a* and 59*b*.

Shown on the screen 54 in FIG. 2A are various options provided by the GUI 53 and selectable by a patient to control his IMD 10 (e.g. the stimulation program it is executing) or to monitor his IMD 10. Just a few typical options are depicted for simplicity that enable the patient to: start or stop stimulation; increase or decrease the amplitude of the stimulation pulses; check IMD monitoring information, such as the battery 36 level, operating status of the IMD, or other data telemetered from the IMD; etc.

External devices such as the RC 50 of FIG. 2A were historically built by the manufacturers of IMDs, and thus were generally dedicated to communicate only with such IMDs. As such, dedicated RC 50 is not freely programmable by a patient, but is instead limited to the IMD functionality provided by the manufacturer, which may be updated from time to time. However, there are many user-programmable commercial mobile devices, such as cell phones, that can provide GUIs and have inherent communication means suitable for functioning as a wireless external controller for an IMD.

FIG. 2B show an example of a mobile device 60 configured for use as an external controller for an IMD, as described in commonly-owned U.S. Patent Application Publication 2015/0073498. The mobile device 60 may be a commercial, multipurpose, consumer device, such as a cell phone, tablet, personal data assistant, laptop or notebook computer, or like device—essentially any mobile, handholdable device capable of functioning as a wireless external controller for an IMD. Examples include the Apple iPhone or iPad, Microsoft Surface, Nokia Lumia devices, Samsung Galaxy devices, and Google Android devices for example.

As shown in FIG. 2B, the mobile device 60 includes a GUI 63 with a screen 64, which may also receive input if it is a touch screen. The mobile device 60 may also have buttons 62 (e.g., a keyboard) for receiving input from the patient, a speaker 66, and a microphone 68. Mobile device 60 further includes a battery (not shown) within its housing 61, which battery may be a primary battery or rechargeable. Mobile device 60 further includes at least one short-range RF antenna 69, and would include telemetry circuitry compliant with a short-range RF standard, such as Bluetooth in one example. Thus, mobile device 60 can inherently communicate via a short-range RF far-field link with an IMD having a short-range RF antenna 42*b*, assuming it is compliant with the Bluetooth standard. Mobile device 60 however is unlikely to contain a coil antenna similar to the coil antenna 59*a* of the RC 50 of FIG. 2B, and thus would be incapable by itself to communicate via a near-field magnetic inductive link with an IMD 10 having only a coil antenna 42*a*. (Mobile device 60 though could be used with other devices or accessories to enable communications with an IMD having a magnetic induction communication coil. See, e.g., U.S. Pat. Nos. 8,983,615 and 9,533,162; U.S. Patent Application Publications 2015/0231402 and 2016/0274752. Mobile device 60 may, in addition to short-range RF communication means enabled by antenna 69, further include longer-range cellular communication means as is well known.

Shown on the screen 64 is a Medical Device Application (MDA) 65, which may reside as microcode in the mobile device 60's microcontroller 67 or which may otherwise be stored in the mobile device's memory. When MDA 65 is executed by the patient (typically by selecting its icon, as explained in the '498 Publication), the microcontroller 67 will configure the mobile device 60 for use as an external controller to communicate with the IMD 10. The MDA 65 includes options selectable by a patient to control his stimulation program or monitor his IMD, similar to what was described earlier with respect to the GUI 53 of the dedicated RC 50 of FIG. 2A. The MDA 65, like other applications executable in the mobile device 60, may have been downloaded using traditional techniques, such as from an Internet server or an "app store." Although not strictly necessary, MDA 65 is logically developed and provided by the manufacturer of the IMD, and may be made available in different versions to work with different mobile device operating systems (e.g., iOS, Android, Windows, etc.).

Both the RC 50 of FIG. 2A and the mobile device 60 of FIG. 2B can thus operate to communicate with an IMD 10 using short-range RF communication means, such as Bluetooth, if the IMD 10 includes a compliant short-range RF antenna 42*b*. However, the inventor perceives problems with this approach, particularly as concerns the IMD 10. In FIG. 1B, the short-range RF antenna 42*b* is included within the IMD's case 30. The case 30 is normally conductive and thus will attenuate wireless communications. This is particularly true if the short-range RF communication standard employs a relatively high frequency such as Bluetooth (e.g., 2.4 GHz). Attenuation using short-range RF communications is further exacerbated by the patient's tissue, although such effects can be mitigated if the IMD 10 is implanted shallowly in the patient and thus nearer to the patient's skin.

A manner of mitigating attenuation would be to include the short-range RF antenna 42*b* in the IMD's header 28. While a short-range RF antenna located in the header 28 would still suffer attenuation of communications related to the patient's tissue, the header material itself would not attenuate as it is formed of non-conductive epoxy. However, it is not a simple matter to put a short-range RF antenna in the IMD's header 28, as the header 28 typically includes very little free space. This is particularly true in an IMD 10 such as that depicted in FIG. 1A, which includes four lead connectors 24. Further, the lead connectors 24 are formed of conductive components (such as header contacts 26 and electrode feedthrough pins 34) which could interfere with communications of a header-based antenna.

The inventor thus proposes a different solution that provides an IMD 10 with a short-range RF antenna such as a Bluetooth antenna which is not significantly attenuated by materials of the IMD 10 itself, but which is not located in the IMD's header.

BRIEF DESCRIPTION OF THE DRAWINGS

FIGS. 1A and 1B respectively show an Implantable Medical Device (IMD) in plan and cross sectional views, in accordance with the prior art.

FIG. 4 shows an improved IMD in a perspective view in which the header and an overcoat for the short-range RF antenna are integrally formed, in accordance with another example of the invention.

FIGS. 5A and 5B show an improved IMD in perspective and cross sectional views in which the external short-range RF antenna is lithographed or printed on the side of the IMD case, in accordance with an example of the invention.

DETAILED DESCRIPTION

An improved Implantable Medical Device (IMD) such as an Implantable Pulse Generator (IPG) is disclosed having a bi-directional short-range far-field Radio-Frequency (RF) data antenna, operable in accordance with a short-range RF standard such as Bluetooth, BLE, NFC, Zigbee, WiFi (802.11x), or MICS. The short-range RF antenna is neither located inside the conductive case of the IMD, nor in the non-conductive header of the IMD that includes the lead connectors. Instead, the short-range RF antenna is outside of the case, proximate to and generally planar with a flat planar side of the case that faces outward of the patient when the IMD is implanted. Dielectric materials keep the antenna from shorting to the case and to the patient's tissue. Because the short-range RF antenna is not located within the conductive case, data communications to and from the antenna are less subject to attenuation. Not locating the antenna in the header reserves room for the header's lead connectors, thus simplifying IMD design.

Figure 3A:
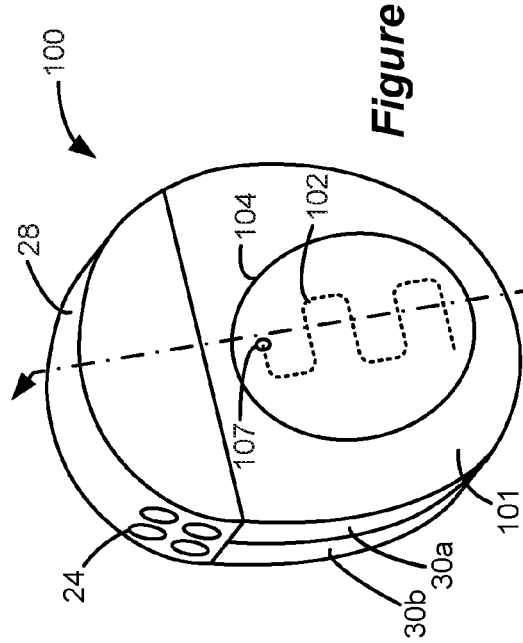
FIGS. 3A and 3B respectively show an improved IMD in perspective and cross sectional views having an external short-range RF antenna affixed to a side of the IMD case, in accordance with an example of the invention.
Figure 3B:
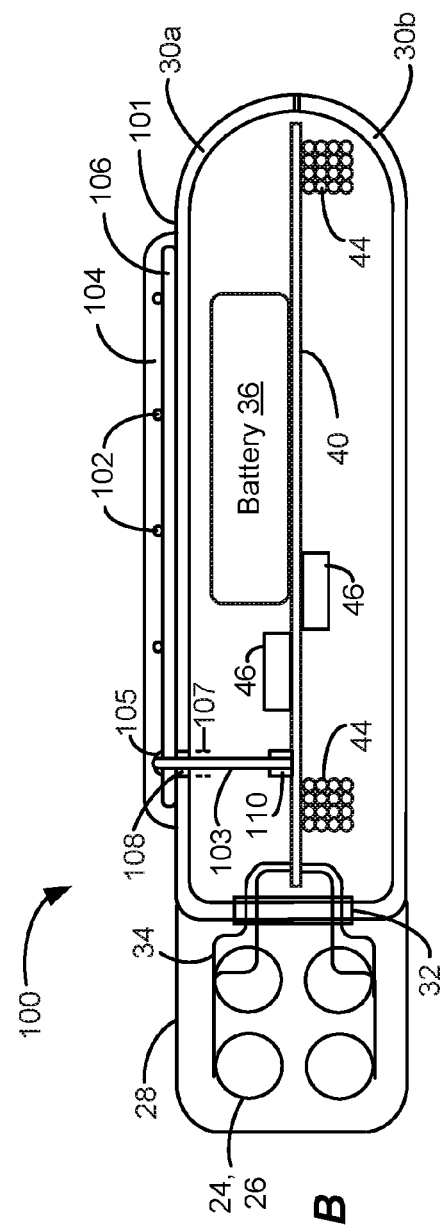

FIGS. 3A and 3B show a first example of the improved IMD 100 in perspective and cross sectional views. IMD 100 includes a short-range RF antenna 102 which is located outside of the conductive case 30 of the IMD 100, but which is not located in its header 28. More specifically, the short-range RF antenna 102 is proximate to and generally planar with one of the flat planar sides 101 of the case 30 (on top case portion 30*a*). Preferably, case side 101 comprises the side of the case 30 that faces outwards from the patient when IMD 100 is implanted. In this manner, communications between the IMD 100 and an external device are not attenuated by the case 30. Because data communications occur to and from the IMD 100 via the short-range RF antenna 102, data antennas internal to the case 30—such as coil antenna 42 and short-range RF antenna 42*b* (FIG. 1B)—are omitted from IMD 100. Omitting such antennas from the inside of the case 30, and from the header 28, is beneficial as it allows the IMD 100 to be made smaller while still reserving room in the header 28 for lead connectors 24.

IMD 100 in the illustrated example includes a charging coil 44 within the case 30 to allow for recharging of battery 36, although as noted earlier battery 36 may also be primary and non-rechargeable, mooting the need for charging coil 44. As shown, case side 101 which carries the short-range RF antenna 102 is on the opposite side of the PCB 40 from the charging coil 44. However, antenna 102 may also be placed on the same side (on the side of bottom case portion 30*b*). Because the inside of the case 30 preferably lacks a data antenna, the structures within the case 30 such as the PCB 40, the battery 36, and the charging coil 44 could be moved to other convenient positions and otherwise integrated in different manners within the case 30.

Figure 2B:
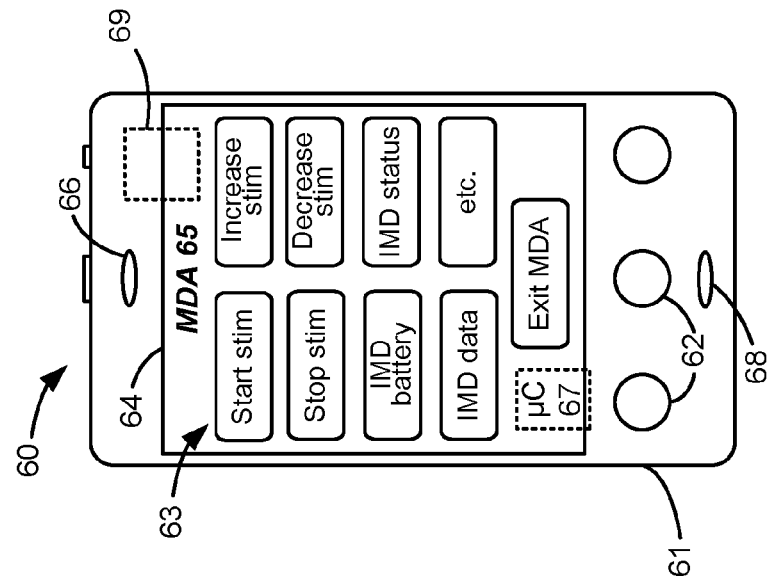
FIGS. 2A and 2B respectively show a dedicated remote control (RC) for communicating with an IMD, and a mobile device for communicating with an IMD, in accordance with the prior art.
Figure 2A:
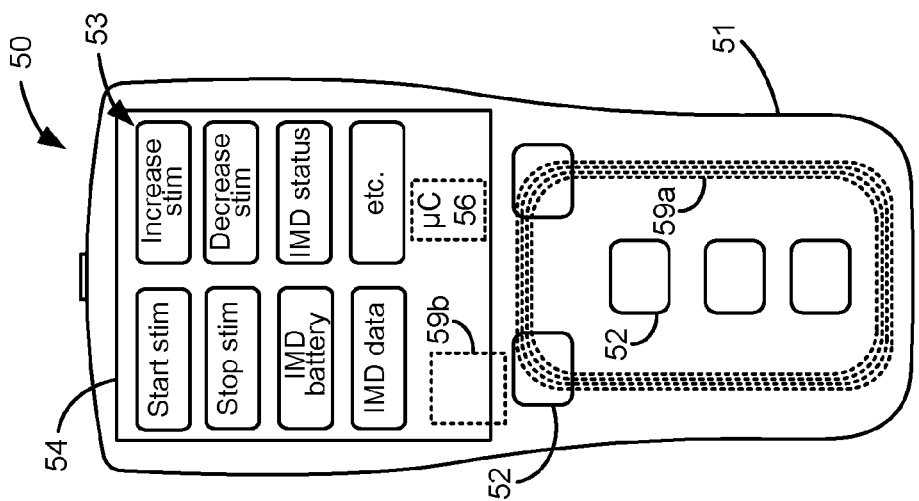

An external device usable to communicate with IMD 100 can for example comprise the remote control (RC) 50 of FIG. 2A or the mobile device 60 of FIG. 2B, assuming that these devices have short range antennas 59*b* and 69 that are compliant with the communication standard employed by the IMD's short-range antenna 102. In a preferred example, the antennas 102, 59*b*, and 69 operate in accordance with the Bluetooth standard, and hence the external device 50 or 60 and the IMD 100 would include telemetry circuitry (e.g., Bluetooth chip sets) operable with that standard.

As shown, short-range RF antenna 102 is serpentine shaped, and has a length that is preferably optimized for the frequency (or frequency range) at which the antenna 102 is designed to operate. For example, Bluetooth communications occur generally at 2.4 GHz (or more specifically in a range of 2.4-2.4835 GHz allowing for the use of 79 1 MHz channels). This frequency (f) equates to a wavelength ($\lambda$) of $\lambda=c/f=12$ cm, where c equal the speed of light ($3*10^8$ m/s). Because the speed of light slows in water ($2.25*10^8$ m/s), with water being the primary component of the patient's tissue, a more accurate wavelength calculation would be on the order of 10 cm. Because short-range RF antenna 102 preferably comprises a monopole quarter-wavelength antenna, the length of the antenna 102 would thus be in the range of 2.5 to 3 centimeters. If this is too long to fit on case side 101 as a straight line, the antenna 102 can be serpentined as shown. However, this is not necessary, and instead the antenna 102 can be straight, or bent into other shapes.

In the example shown, short-range RF antenna 102 is formed of a conductive wire, although patch and slot antennas could also be used. As best shown in FIG. 3B, to insulate the antenna 102 from the case 30 (which is normally grounded), a dielectric material 106 is included between the antenna 102 and the case side 101. Dielectric material 106 could comprise different materials (plastics, ceramics, etc.), but in a preferred example comprises a thin layer of glass. Such glass material may comprise a thin film, or may be vapor deposited in the location that the antenna 102 will occupy on the case side 101. The conductive material of the case 30, which again is normally grounded, can act as a ground plane for antenna 102.

An antenna feedthrough pin 103 passes through a hole 107 in the case side 101 and couples to the PCB 40, and in particular to short-range RF telemetry circuitry. PCB 40 may include a pre-soldered socket 110 to assist in coupling the antenna feedthrough pin 103 to the PCB 40. A glass ferrule 108 is positioned in hole 107, which ferrule 108 includes its own hole for passage of the antenna feedthrough pin 103. The antenna feedthrough pin 103 can be connected to the short-range RF antenna 102 via a weld 105, which preferably comprises a laser weld.

Once the antenna feedthrough pin 103 is so positioned, the top case portion 30a can be heated to sinter (melt) the glass ferrule 108 to ensure a hermetic seal between the inside and outside of the case 30 at hole 107. Sintering can also further melt the dielectric material 106 to add further hermeticity at the location of the hole 107 if dielectric material 106 is meltable. Although not shown, hole 107 may include a more-complex feedthrough structure similar in nature to the electrode feedthrough 32 used to hermetically pass the electrode feedthrough pins 34 between the inside and outside of the case 30.

A dielectric overcoat 104 is formed over the short-range RF antenna 102 to further ensure good hermeticity, and to insulate the antenna 102 from the patient's tissue. In a preferred example, dielectric overcoat 104 comprises epoxy, and may comprise the same epoxy used to form the header 28. In fact, the header 28 and dielectric overcoat 104 may be molded over the lead connector 24 and the short-range RF antenna 102 at the same time. Further, header 28 and dielectric overcoat 104 may be formed as a single contiguous overmold, as shown in FIG. 4.

With the various components of IMD 10 introduced, its assembly can now be summarized. Construction preferably begins with top case portion 30a to which the short-range RF antenna 102 will be affixed. The top case portion 30a is preferably formed with the dielectric material 106 in place on the case side 101. The ferrule 108 is positioned within hole 107 and the antenna feedthrough pin 103 is passed through the ferrule 108 and the dielectric material 106 such that it protrudes above the dielectric material 106. The top case portion 30a with these components is then heated (sintered) to melt the ferrule 108 to the hole 107 and to the antenna feedthrough pin 103, and possibly also to melt and (better) adhere the dielectric material 106 to the case side 101.

At this point, the short-range RF antenna 102, preferably pre-formed with the appropriate length and shape, can be connected to the top of the antenna feedthrough pin 103 such that it rests on the top of the dielectric material 106. However, connection of the antenna 102 to the antenna feedthrough pin 103 can also occur after the case is seales, as explained below. Dielectric overcoat 104 can be added on top of the antenna 102 at this stage, or later as explain below.

In a separate assembly step, an electronics assembly is formed. This can begin by constructing an electrode feedthrough subassembly in which the electrode feedthrough pins 34 are formed and sintered through the electrode feedthrough 32, and then the lead connectors 24 and header contacts 26 are connected to first ends of the electrode feedthrough pins 34. The second ends of the electrode feedthrough pins 34 can then be soldered to be PCB 40, which PCB 40 has otherwise been completed with its components pre-attached (e.g., the charging coil 44, the battery 36, the antenna feedthrough pin socket 110, and various circuitry 46).

With the electronics assembly completed in this fashion, the electronic assembly can be placed in the bottom case portion 30b with the edge of the bottom case portion 30b meeting with the edge of the electrode feedthrough 32. Then, the top case portion 30a constructed as described above can be placed over the bottom case portion 30b and the electrode feedthrough 32, at which point the end of the antenna feedthrough pin 103 can be press fit into the socket 110 on the PCB 40. The case 30 may then be sealed by laser welding the case portions 30a and 30b to each other, and by welding each case portion to the electrode feedthrough 32. The antenna 102 can be connected to the antenna feedthrough pin 103 at this point if this did not occur earlier.

Thereafter, the header 28 can be molded over the lead connectors 24, and as mentioned above, this step may also include formation of the dielectric overcoat 104, either as a structure separate from the header 28 (FIG. 3A), or as integrated with the header (FIG. 4).

Short-range RF antenna 102 may be formed in other manners. For example, although not illustrated, the wire comprising antenna 102 can be bent at one end and passed through the hole 107 for connection to the PCB 40. In other words, this end of the antenna wire would be sintered in hole 107, and a separate antenna feedthrough pin 103 could be dispensed with.

Further, short-range RF antenna need not comprise a wire, but instead could comprise a lithographed or printed antenna. For example, and as shown in the IMD 100' of FIGS. 5A and 5B, antenna 102 could be formed by sputtering/etching or printing a conductive material (e.g., conductive ink) directly on the dielectric material 106 in contact with the case side 101. If necessary this printed or lithographed antenna 102 could be soldered, welded or otherwise connected (105) to antenna feedthrough pin 103 to ensure good connectivity to the PCB 40 and its short-range RF telemetry circuitry.

Figure 6A:
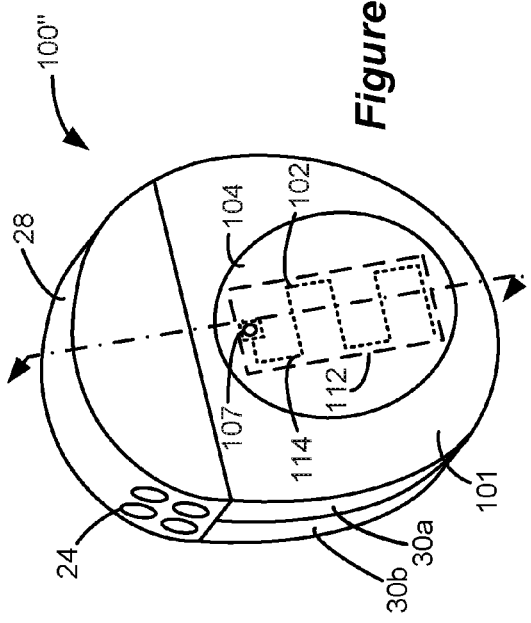
FIGS. 6A and 6B show an improved IMD in perspective and cross sectional views in which the external short-range RF antenna is pre-formed on a substrate affixed to the side of the IMD case, in accordance with an example of the invention.
Figure 6B:
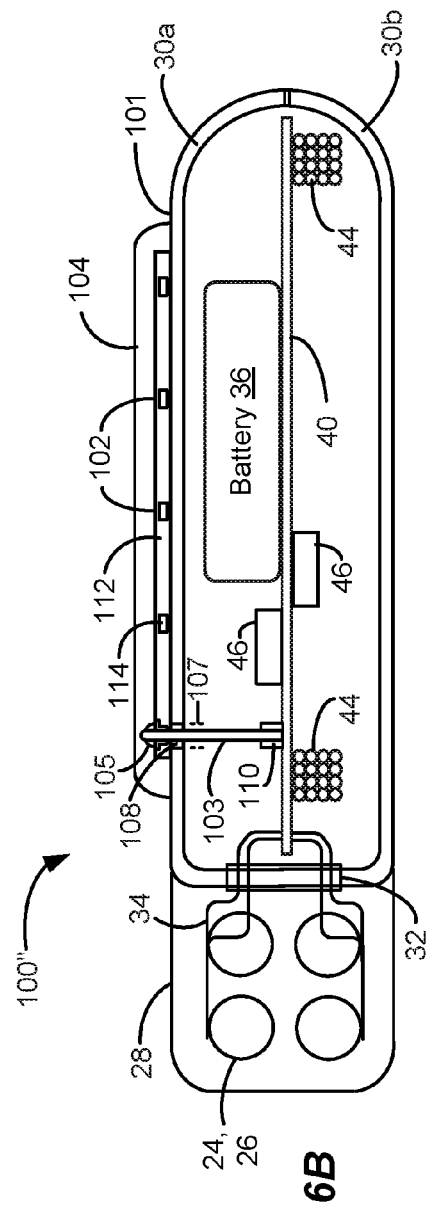

In another alternative shown in the IMD 100" of FIGS. 6A and 6B, the short-range RF antenna 102 can be pre-formed in or on a substrate 112, such as a printed circuit board (PCB). Substrate 112 could be placed over the dielectric material 106, but if the bottom surface of the substrate 112 is insulative, use of the dielectric material 106 can be omitted as shown in FIG. 6B because this bottom surface will prevent shorting of the antenna 102 to the case side 101. In the example shown, the antenna 102 is formed as a patterned trace in an inner conductive layer of the substrate 112. However, in other examples, the antenna 102 can be patterned on top of the substrate 112. Although in this example the antenna 102/substrate 112 would not be insulated on its top surface, the antenna 102 would still eventually be insulated by application of the dielectric overcoat 104.

Although particular embodiments have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:
1. An implantable medical device, comprising:
a conductive case comprising electronic circuitry inside the case, wherein the case comprises a planar side;
a header affixed to the case, wherein the header comprises at least one lead connector configured to receive an electrode lead;
a short-range far-field Radio-Frequency (RF) data antenna outside of the case, wherein the data antenna is proximate to and planar with the planar side of the case; and
a dielectric overcoat over the data antenna outside of the case, wherein the dielectric overcoat and the header are contiguous and formed of the same material.

2. The implantable medical device of claim 1, wherein the data antenna comprises a monopole antenna, and wherein the conductive case is grounded and acts as a ground plane for the monopole antenna.

3. The implantable medical device of claim 1, further comprising a dielectric material outside the case and between the data antenna and the planar side of the case.

4. The implantable medical device of claim 1, further comprising an electrode feedthrough configured to pass at least one electrode feedthrough pin from the inside to an outside of the case, wherein the at least one electrode pin is coupled to the electronic circuitry, wherein the lead connector comprises at least one header contact, wherein each at least one header contact is connected outside the case to one of the at least one feedthrough pins.

5. The implantable medical device of claim 1, further comprising a hole in the planar side of the case, wherein the data antenna is coupled to the electronic circuitry through the hole.

6. The implantable medical device of claim 5, further comprising an antenna feedthrough pin passing through the hole and comprising a first end and a second end, wherein the antenna feedthrough pin is connected at the first end to the electronic circuitry and is connected outside of the case at the second end to the data antenna.

7. The implantable medical device of claim 6, wherein the antenna feedthrough pin is sintered within the hole to provide a hermetic seal between the inside and outside of the case.

8. The implantable medical device of claim 1, wherein the dielectric overcoat and the header are formed at the same time.

9. The implantable medical device of claim 1, wherein the data antenna comprises a wire.

10. The implantable medical device of claim 1, wherein the data antenna is serpentined.

11. The implantable medical device of claim 1, wherein the data antenna comprises a patch or slot antenna.

12. The implantable medical device of claim 1, wherein the data antenna comprises a lithographed or printed data antenna.

13. The implantable medical device of claim 12, further comprising a dielectric material in contact with the planar side of the case, where the data antenna is lithographed or printed on the dielectric material.

14. The implantable medical device of claim 1, wherein the data antenna is configured to operate in accordance with a wireless communication standard comprising one or more of Bluetooth, BLE, NFC, Zigbee, WiFi, and MICS.

15. The implantable medical device of claim 1, further comprising:
a substrate outside of the case, wherein the short-range far-field Radio-Frequency (RF) data antenna is preformed in or on the substrate, wherein the substrate is proximate to and planar with the planar side of the case,
wherein the dielectric overcoat is over the substrate and data antenna outside of the case.

16. The implantable medical device of claim 15, wherein the substrate is in contact with the planar side of the case.

17. The implantable medical device of claim 15, further comprising a hole in the planar side of the case, wherein the data antenna is coupled to the electronic circuitry through the hole.

18. The implantable medical device of claim 17, further comprising an antenna feedthrough pin passing through the hole and comprising a first end and a second end, wherein the antenna feedthrough pin is connected at the first end to the electronic circuitry and is connected outside of the case at the second end to the data antenna, wherein the antenna feedthrough pin is sintered within the hole to provide a hermetic seal between the inside and outside of the case.

\* \* \* \* \*